US012380584B2

(12) United States Patent
Hendriks et al.

(10) Patent No.: US 12,380,584 B2
(45) Date of Patent: Aug. 5, 2025

(54) ACCURATE DIAPHRAGM THICKNESS AND FUNCTION EVALUATION USING ULTRASOUND AND MECHANICAL VENTILATOR SIGNALS

(71) Applicant: KONINKLIJKE PHILIPS N.V., Eindhoven (NL)

(72) Inventors: Cornelis Petrus Hendriks, Eindhoven (NL); Roberto Buizza, Eindhoven (NL); Michael Polkey, London (GB); Jaap Roger Haartsen, Eindhoven (NL); Joerg Sabczynski, Hamburg (DE); Rafael Wiemker, Hamburg (DE); Thomas Koehler, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 158 days.

(21) Appl. No.: 18/213,286

(22) Filed: Jun. 23, 2023

(65) Prior Publication Data

US 2023/0419527 A1 Dec. 28, 2023

Related U.S. Application Data

(60) Provisional application No. 63/354,824, filed on Jun. 23, 2022.

(51) Int. Cl.
*G06T 7/60* (2017.01)
*A61B 8/00* (2006.01)
(Continued)

(52) U.S. Cl.
CPC .............. *G06T 7/60* (2013.01); *A61B 8/08* (2013.01); *A61B 8/4236* (2013.01);
(Continued)

(58) Field of Classification Search
CPC .............. G06T 7/60; G06T 7/0012; G06T 2207/10132; G06T 2207/30004;
(Continued)

(56) References Cited

U.S. PATENT DOCUMENTS 3,946,729 A * 3/1976 Hanna .................. A61B 5/08
128/204.23
4,444,201 A * 4/1984 Itoh .................... A61M 16/021
128/204.23
(Continued)

OTHER PUBLICATIONS

DiNino, Ernest, et al. "Diaphragm ultrasound as a predictor of successful extubation from mechanical ventilation." Thorax 69.5 (2014): 431-435. (Year: 2014).*
(Continued)

*Primary Examiner* — Sean D Mattson
(74) *Attorney, Agent, or Firm* — Daniel H. Brean (57) ABSTRACT

A diaphragm measurement device includes at least one electronic processor programmed to perform a diaphragm measurement method including receiving ultrasound imaging data of a dimension of a diaphragm of a patient during inspiration and expiration while the patient undergoes mechanical ventilation therapy with a mechanical ventilator; receiving respiratory data of the patient during inspiration and expiration while the patient undergoes the mechanical ventilation therapy; calculating a diaphragm thickness metric based on the received ultrasound imaging data of the diaphragm of the patient and the received respiratory data; and displaying, on a display device, a representation of the calculated diaphragm thickness metric.

9 Claims, 5 Drawing Sheets

(51) Int. Cl.
*A61B 8/08* (2006.01)
*A61M 16/00* (2006.01)
*G06T 7/00* (2017.01)
*A61B 5/085* (2006.01)

(52) U.S. Cl.
CPC ....... *A61M 16/0003* (2014.02); *G06T 7/0012* (2013.01); *A61B 5/085* (2013.01); *A61M 2016/0027* (2013.01); *A61M 2016/003* (2013.01); *G06T 2207/10132* (2013.01); *G06T 2207/30004* (2013.01)

(58) Field of Classification Search
CPC ....... A61B 8/08; A61B 8/4236; A61B 8/5223; A61B 8/0858; A61B 8/486; A61B 5/085; A61B 5/097; A61B 5/1072; A61B 5/087; A61B 5/091; A61M 16/0003; A61M 16/024; A61M 2016/0027; A61M 2016/003; A61M 2016/0036; A61M 2230/46; G16H 20/40; G16H 40/63
See application file for complete search history.

(56) References Cited

U.S. PATENT DOCUMENTS

| | | | | |
|---|---|---|---|---|
| 5,448,995 A | * | 9/1995 | Yost ..................... | A61B 8/0858 600/443 |
| 2018/0256075 A1 | * | 9/2018 | Souzy .................. | A61B 5/6823 |
| 2023/0414889 A1 | * | 12/2023 | Haartsen ................ | G16H 30/20 |

OTHER PUBLICATIONS

Umbrello, Michele, et al. "Diaphragm ultrasound as indicator of respiratory effort in critically ill patients undergoing assisted mechanical ventilation: a pilot clinical study." Critical Care 19 (2015): 1-10. (Year: 2015).*
International Search Report for PCT/EP2023/067161 filed Jun. 23, 2023.
Pirompanich, P. et al., "Use of diaphragm thickening fraction combined with rapid shallow breathing index for predicting success of weaning from mechanical ventilator in medical patients", Journal of Intensive Care, London, UK, vol. 6, No. 1, (Feb. 2, 2018), pp. 1-7.
Blumhof, S. et al., "Change in Diaphragmatic thicknes during the respiratory cycle predicts extubation success at various levels of pressure support ventilation", Lung, NY, vol. 194, No. 4, (Jul. 15, 2016), pp. 519-525.
Eksombatchai. D. et al., "The ratio of respiratory rate to diaphragm thickening fraction for predicting extubation success", BMC Pulmonary Medicine, London, UK, vol. 23, No. 1 (Apr. 4, 2023), pp. 1-10.
Oppersma, E. et al., "Functional assessment of the diaphragm by speckle tracking ultrasound during inspiratory loading." J Appl Phys. 123: 1063-1070 (2017).
Goligher, E.C., et al. "Measuring diaphragm thickness with ultrasound in mechanically ventilated patients: feasibility, reproducibility and validity". Intensive Care Med. Apr. 2015:41(4):642-9. doi: 10.1007/s00134-015-3687-3. Epub Feb. 19, 2015.
"Diaphragm function in patients with interstitial lung disease (ILD): a pilot study." Research Square. (2022).
Tuinman, P.R. et al., "Respiratory muscle ultrasonography: methodology, basic and advanced principles and clinical applications in ICU and ED patients—a narrative review". Intensive Care Med. Apr. 2020;46(4):594-605.
O'Hara, D.N. et al., "Ultrasonographic modelig of diaphragm function: A novel approach to respiratory assessment". PLos One 15(3):): e0229972. https://doi.org/10.1371/journal.pone.0229972.

* cited by examiner

ACCURATE DIAPHRAGM THICKNESS AND FUNCTION EVALUATION USING ULTRASOUND AND MECHANICAL VENTILATOR SIGNALS

The following relates generally to the respiratory therapy arts, mechanical ventilation arts, ventilator induced lung injury (VILI) arts, mechanical ventilation weaning arts, and related arts.

BACKGROUND

Diaphragmatic ultrasonography (US) allows for quantification of diaphragm thickness, strain (rate) and excursion, and with this also the respiratory rate and duration of each contraction. Diaphragm thickness (expressed as thickening fraction) and strain reflect contractile activity and correlate well with diaphragmatic electrical activity and diaphragmatic pressure. Consequently, thickness and strain may be used as a surrogate for respiratory effort. Applications of diaphragmatic ultrasound include assessment of diaphragm function, atrophy detection, weaning prediction, and mechanical ventilation (MV) setting management. Other applications could be asynchrony detection and proportional ventilation (non-invasive neurally adjusted ventilatory assist (NAVA)). The use of diaphragmatic ultrasound in mechanical ventilation is gaining attention and therefore, technical problems and use cases are currently being investigated.

A diaphragm thickening fraction (TFdi or TFDI) as measured by ultrasound (US) are carried out by an operator who looks at the patient and takes an ultrasound image at end inhalation and end exhalation. The diaphragm thickness fraction is determined by subtracting the end inhalation thickness from the end exhalation thickness and dividing the difference by the exhale thickness according to Equation 1:

$$TFdi = \frac{T_{ei} - T_{ee}}{T_{ee}} * 100\% \quad (1)$$

with $T_{ei}$ as the end-inspiratory thickness.

Some studies have evaluated the correlation between TFdi and respiratory effort. In one study (see, e.g., E. Oppersma et al. Functional assessment of the diaphragm by speckle tracking ultrasound during inspiratory loading. J Appl Phys. 2017), at the zone of apposition the diaphragm strain can similarly be measured in real-time. For example, in this study, the functional assessment of the diaphragm by speckle tracking ultrasound during inspiratory loading was analyzed. The technique of speckle tracking ultrasound allows for the detection and tracking of diaphragmatic strain over time by analyzing acoustic markers called speckles. These speckles are formed by interference of ultrasound waves that are scattered from physical structures of a size comparable to the wavelength of the ultrasound waves. Both diaphragm strain and diaphragm strain rate were highly correlated to transdiaphragmatic pressure Pdi (strain $r^2=0.72$; strain rate $r^2=0.80$) and diaphragm electrical activity EAdi (strain $r^2=0.60$; strain rate $r^2=0.66$).

A problem is the reliability of the diaphragmatic thickness measurements. The accuracy, repeatability, and reproducibility are limited due to the thin form factor of the diaphragm, the motion and macro-deformation of the diaphragm and the surrounding structures and tissues, the device handling (angle, position, motion), poor image quality, and operator skills. The variation and uncertainty in TFDI can be very high (see, e.g., Goligher E C, et al. 2015, "Measuring diaphragm thickness with ultrasound in mechanically ventilated patients: feasibility, reproducibility and validity". Intensive Care Med. 2015 April; 41(4):642-9. doi: 10.1007/s00134-015-3687-3. Epub 2015 Feb. 19. Erratum in: Intensive Care Med. 2015 April; 41(4):734. Sebastien-Bolz, Steffen [corrected to Bolz, Steffen-Sebastien]. PMID: 25693448; Tuinman P R, et al., 2020, "Respiratory muscle ultrasonography: methodology, basic and advanced principles and clinical applications in ICU and ED patients—a narrative review". Intensive Care Med. 2020 April; 46(4):594-605. doi: 10.1007/s00134-019-05892-8. Epub 2020 Jan. 14. PMID: 31938825; PMCID: PMC7103016). For example, Goligher reports a thickness change 0.3 mm±0.3 mm. In this example the error margin (0.6 mm) is twice the nominal thickness change (0.3 mm). This uncertainty undermines the confidence in clinical decisions which are based on the TFDI, for example decisions on pressure support, weaning, and extubation (see, e.g., Tuinman,).

Besides the above-mentioned measurement errors, another source of variability in TFDI is the variation in respiratory effort/work of breathing (WOB) between breaths. This is reflected in the ventilator waveforms which vary over time. If the TFDI is measured and averaged over different breaths, without considering the variability in WOB, this obviously contributes to the error margin in TFDI.

A further source of anticipated variation in practice is disease induced diaphragm atrophy which is likely to make the 'noise to signal' ratio higher.

Another study (see, e.g., O'Hara D N, et al., 2020, "Ultrasonographic modeling of diaphragm function: A novel approach to respiratory assessment". PLoS ONE 15(3): e0229972. https://doi.org/10.1371/journal.pone.0229972) measured the diaphragm thickness Tdi at different levels of negative inspiratory force (NIF) using a handheld NIF meter. A NIF meter determines the strength of the respiratory muscles by recording the negative airway pressure which is generated while the patient is making a breathing attempt through a mouthpiece with a closed valve. Tdi was measured with an ultrasound probe at expiration, NIF=−30 cmH$_2$O, NIF=−60 cmH2O, and maximum NIF. A quadratic function was used to fit the relation between NIF and Tdi. O'Hara suggests that the statistical function has the potential to predict the maximum NIF based on ultrasound measurements. The advantage is to eliminate patient factors that may otherwise limit NIF measurements, such as the ability to form a tight seal at the lips or follow the respiratory technician's instructions, or in those with a depressed mental or neurological status.

The following discloses certain improvements to overcome these problems and others.

SUMMARY

In one aspect, a diaphragm measurement device includes at least one electronic processor programmed to perform a diaphragm measurement method including receiving ultrasound imaging data of a dimension of a diaphragm of a patient during inspiration and expiration while the patient undergoes mechanical ventilation therapy with a mechanical ventilator; receiving respiratory data of the patient during inspiration and expiration while the patient undergoes the mechanical ventilation therapy; calculating a diaphragm thickness metric based on the received ultrasound imaging data of the diaphragm of the patient and the received respiratory data; and displaying, on a display device, a representation of the calculated diaphragm thickness metric.

In another aspect, a diaphragm measurement method includes, with at least one electronic controller: receiving ultrasound imaging data of a dimension of a diaphragm of a patient during inspiration and expiration while the patient undergoes mechanical ventilation therapy with a mechanical ventilator; receiving respiratory data of the patient during inspiration and expiration while the patient undergoes the mechanical ventilation therapy; calculating a diaphragm thickness metric based on the received ultrasound imaging data of the diaphragm of the patient and the received respiratory data; and displaying, on a display device, a representation of the calculated diaphragm thickness metric.

One advantage resides in facilitating the weaning of patients off of mechanical ventilation therapy.

Another advantage resides in using a ventilator waveform to a reduce an error margin in a diaphragm thickness estimation.

Another advantage resides in determining a respiratory function based on a correlation between the ventilator waveform and the diaphragmatic thickness change.

Another advantage resides in determining a sedation level based on a correlation between the ventilator waveform and the diaphragmatic thickness change.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

As used herein, the singular form of "a," "an," and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

Figure 1:
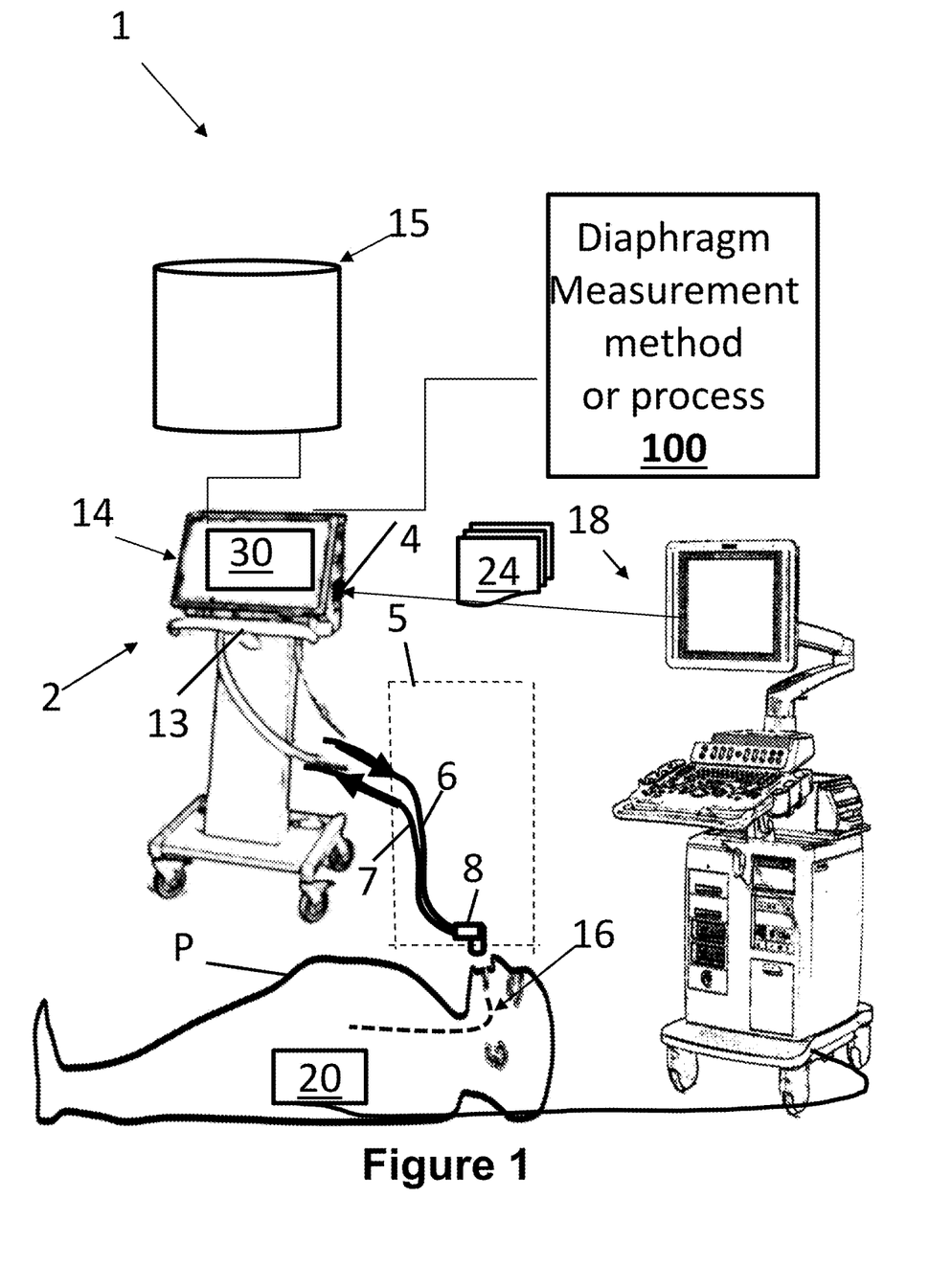
FIG. 1 diagrammatically shows an illustrative diaphragm measurement device in accordance with the present disclosure.

With reference to FIG. 1, a diaphragm measurement device 1 is shown. A mechanical ventilator 2 is configured to provide ventilation therapy to an associated patient P is shown. As shown in FIG. 1, the mechanical ventilator 2 includes an outlet 4 connectable with a patient breathing circuit 5 to delivery mechanical ventilation to the patient P. The patient breathing circuit 5 includes typical components for a mechanical ventilator, such as an inlet line 6, an optional outlet line 7 (this may be omitted if the ventilator employs a single-limb patient circuit), a connector or port 8 for connecting with an endotracheal tube (ETT) 16, and one or more breathing sensors (not shown), such as a gas flow meter, a pressure sensor, end-tidal carbon dioxide (etCO$_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT. The mechanical ventilator 2 also includes at least one electronic processor or controller 13 (e.g., an electronic processor or a microprocessor), a display device 14, and a non-transitory computer readable medium 15 storing instructions executable by the electronic controller 13.

FIG. 1 diagrammatically illustrates the patient P intubated with an ETT 16 (the lower portion of which is inside the patient P and hence is shown in phantom). The connector or port 8 connects with the ETT 16 to operatively connect the mechanical ventilator 2 to deliver breathable air to the patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the patient P receives breathable gas enriched with oxygen, or so forth.

FIG. 1 also shows a medical imaging device 18 (also referred to as an image acquisition device, imaging device, and so forth). As primarily described herein, the medical imaging device 18 comprises an ultrasound (US) medical imaging device 18. The illustrative embodiments employ brightness mode (B-mode) ultrasound imaging to assess the diaphragm thickness metric. However, other types of ultrasound imaging or data are contemplated, such as motion mode (M-mode) data collected as a single ultrasound line over a time interval, or so forth.

In a more particular example, the medical imaging device 18 includes an ultrasound patch 20 that is wearable by the patient P (e.g., on the abdomen or chest of the patient P in position to image the diaphragm of the patient, as shown in FIG. 1). The US patch 20 is positioned to acquire US imaging data (i.e., US images) 24 of the diaphragm of the patient P. For example, the US patch 20 is configured to acquire imaging data of a diaphragm of the patient P, and more particularly US imaging data related to a thickness of the diaphragm of a patient P during inspiration and expiration while the patient P undergoes mechanical ventilation therapy with the mechanical ventilator 2. The electronic processor 13 controls the ultrasound imaging device 18 to receive the ultrasound imaging data 24 of the diaphragm of the patient P from the US patch 20. Although only one US patch 20 is shown in FIG. 1, it will be appreciated that any suitable number of patches can be attached to the patient P. The ultrasound patch(es) 20 allow for continuous and automatic acquisition of the diaphragm thickness data (Tdi) from the acquired ultrasound imaging data 24.

The non-transitory computer readable medium 15 stores instructions executable by the electronic controller 13 to perform a diaphragm measurement method or process 100.

Figure 2:
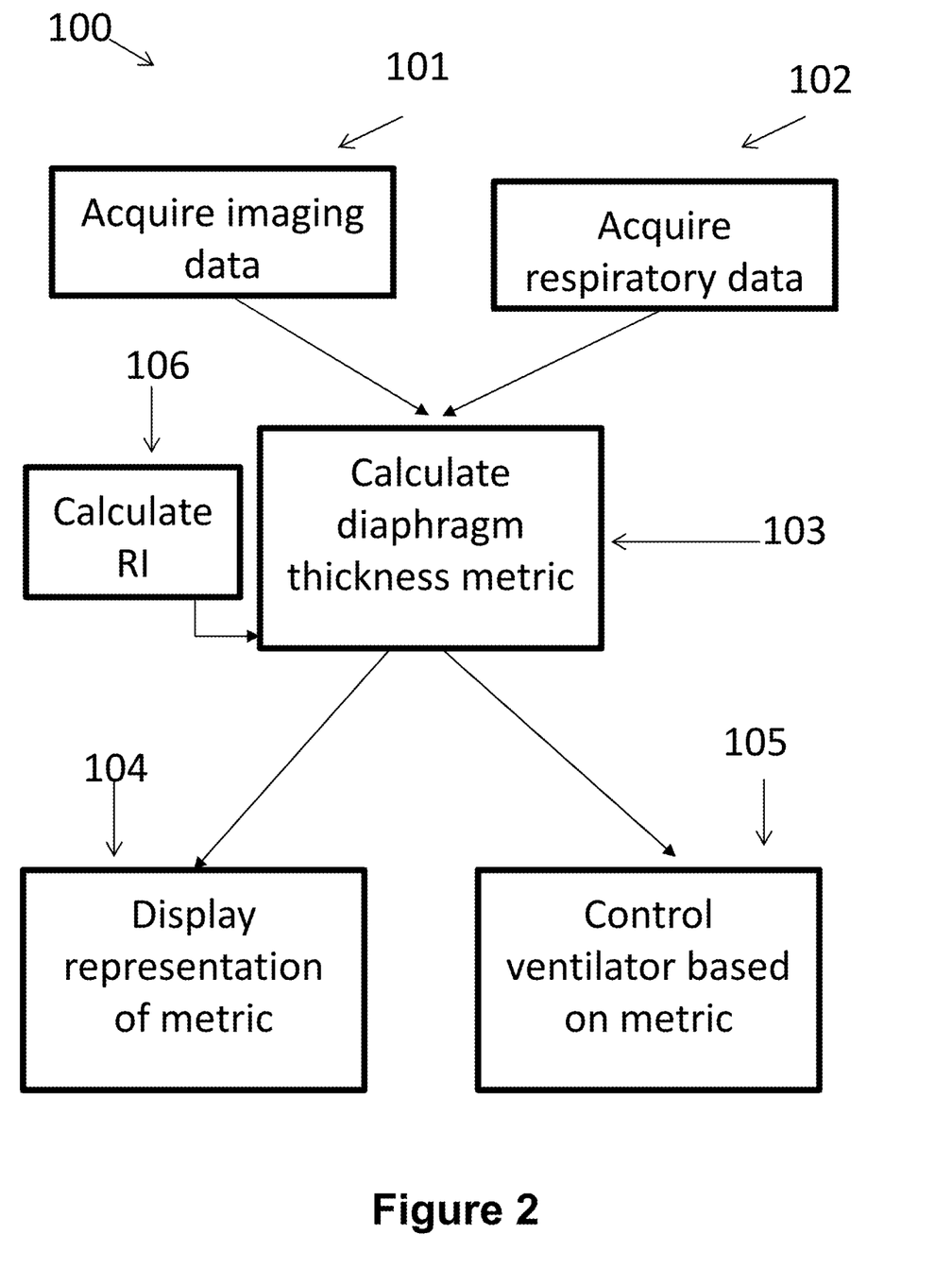
FIG. 2 shows example flow charts of operations suitably performed by the system of FIG. 1.

With reference to FIG. 2, and with continuing reference to FIG. 1, an illustrative embodiment of the diaphragm measurement method 100 is diagrammatically shown as a flowchart. At an operation 101, the US imaging data 24 of the diaphragm of the patient P is received during inspiration and expiration while the patient undergoes mechanical ventilation therapy with the mechanical ventilator 2. To do so, the electronic controller 13 can control the ultrasound patch 20 to acquire the ultrasound imaging data 24 and receive the ultrasound imaging data 24 of the diaphragm of the patient P from the ultrasound patch 20. These images are not necessarily acquired while the patient P is on mechanical ventilation, but instead may be acquired (for example) prior to intubation of the patient.

At an operation 102, respiratory data of the patient P during inspiration and expiration is received while the patient undergoes the mechanical ventilation therapy with the mechanical ventilator 2. The respiratory data of the patient P can include one or more of an airway pressure in an airway of the patient P or an airway flow in an airway of the patient P measured during ventilation therapy by the mechanical ventilator 2. In some examples, the respiratory data of the patient P can include a mean airway pressure value or a mean airway flow value at an end of inspiration and an end of expiration. In other examples, the respiratory data of the patient P can a maximum airway pressure or airway flow value and a minimum airway pressure or airway flow value at an end of inspiration and an end of expiration. It will be appreciated that the image acquisition operation 101 and the respiratory data operation 102 can be performed in any suitable order, or concurrently.

At an operation 103, a diaphragm thickness metric can be calculated based on the received US imaging data 24 of the diaphragm of the patient P and the received respiratory data. In one example, the diaphragm thickness metric includes a diaphragm thickening ratio indicative of a diaphragm thickness during inspiration relative to a diaphragm thickness during expiration. In another example, the diaphragm thickness metric includes a mean diaphragm thickness over multiple respiratory cycles.

To calculate the diaphragm thickness metric, the electronic controller 13 is configured to receive a Tdi signal from the ultrasound imaging data 24 and the pressure p (or flow v) signal from the mechanical ventilator 2. The electronic controller 13 applies a regression analysis to estimate a relation (e.g., a function, a model, and so forth) between the Tdi signal and the pressure or flow data (i.e., Tdi=f(p) or Tdi=f(v). From this relation, the electronic controller 13 is configured to determine $Tdi_{expiration}=f(p_{expiration})$ (i.e., the relation at expiration) and $Tdi_{inspiration}=f(p_{inspiration})$ (i.e., the relation at inspiration), and subsequently a diaphragmatic thickness change ΔTdi, and a diaphragm thickening fraction TFDI as the diaphragm thickness metric. The input values $p_{inspiration}$ and $p_{expiration}$ can be the minimum and maximum recorded airway pressures, or the mean airway pressures at inspiration and expiration (for example the mean of 10 or 100 subsequent cycles).

Figure 3:
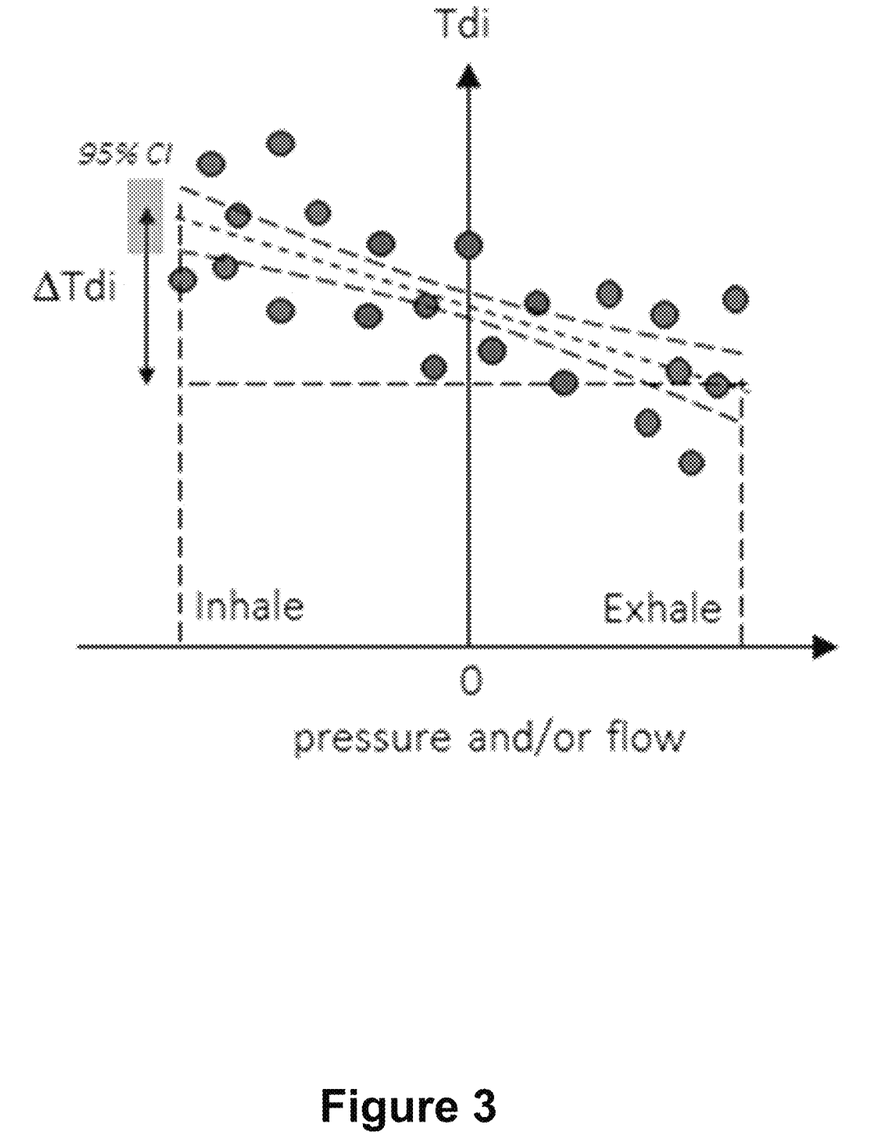
FIGS. 3, 4, 5A, and 5B show data sets for generating a diaphragmatic thickness metric using the device of FIG. 1.
Figure 4:
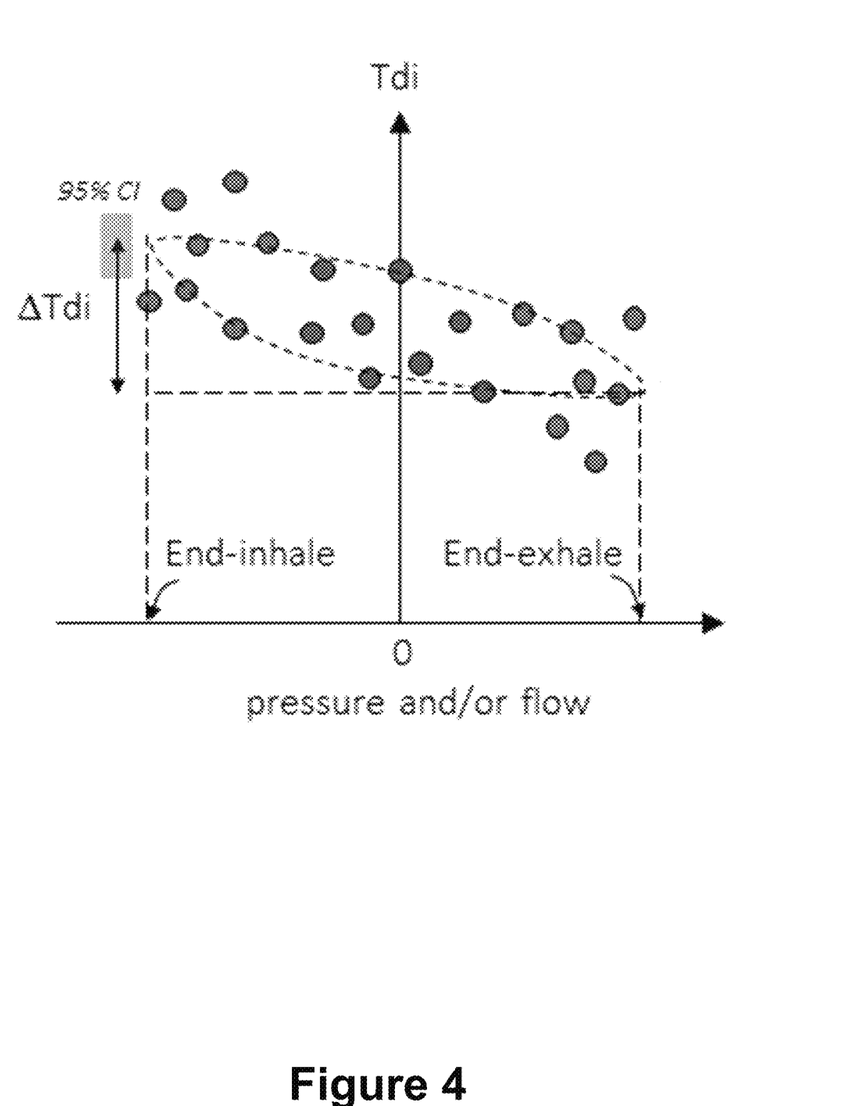

FIGS. 3 and 4 show examples of generating the diaphragm thickness metric. FIG. 3 shows an example of determining a diaphragmatic thickness change (ΔTdi). The example shown in FIG. 3 displays the diaphragm thickness data Tdi as a function of the ventilator waveform (i.e., pressure p or flow v depending on which is the respiration data received at the operation 102) relative to the diaphragmatic thickness change ΔTdi. A confidence interval (shown in FIG. 3 as a shaded bar and having a value of 95%) can be reduced due to (1) more data points are acquired with the ultrasound patch 20, (2) intermediate data points are acquired (central dots shown in FIG. 3), (3) the inhale and exhale points are determined more precisely, i.e., from the ventilator waveform instead of by looking at the patient P or the ultrasound imaging data 24, and (4) by taking into account the cycle-to-cycle variation, i.e. the inhale and/or exhale pressures and volumes vary between breaths. FIG. 4 shows an alternative example, in which two functions (one during inhalation and one during exhalation) can be fitted.

In some embodiments, the regression analysis can be a linear regression analysis as the relation between Tdi and the pressure p (or the flow v) as a straight line with a slope S according to Equation (2):

$$S=\Delta Tdi/\Delta p \text{ or } S=\Delta Tdi/\Delta v \qquad (2)$$

In some embodiments, the diaphragmatic thickness change ΔTdi can be divided by a mean thickness at inhale or exhale (i.e., the diaphragm thickening fraction TFDI). The advantage of using TFDI is that the slope becomes less sensitive to changes in mean thickness over time for example due to atrophy.

In other embodiments, a logarithm of the thickness can be used to calculate the diaphragm thickness metric, because then the slope is invariant against changes of the mean thickness (i.e., any factor becomes a fix offset in log scale).

Referring back to FIG. 2, at an operation 104, a representation 30 of the calculated diaphragm thickness metric is displayed on the display device 14 of the mechanical ventilator 2. In some examples, when multiple ultrasound patches 20 are attached to different locations on the chest of the patient P, the representation 30 can include a color map showing distribution of activity of the diaphragm.

In some embodiments, the diaphragm thickness metric can be calculated as a ratio of a diaphragmatic thickness of the diaphragm and one of an airway pressure or airway flow in an airway of the patient P. In such embodiments, the ratio of the diaphragmatic thickness of the diaphragm and one of the airway pressure or airway flow in the airway of the patient P comprises a compliance of the airway of the patient P.

The slope S of the linear regression relation provides insight in the behavior and effectiveness of the diaphragm muscle activity as a function of the MV support of the patient P and sedation therapy of the patient P. The slope S can be displayed as the indication 30 on the display device 14 of the mechanical ventilator 2. This relation S is more informative then a single TFDI point without any further reference or information. The diaphragmatic thickness change ΔTdi reflects the patient effort ("input"), while the airway pressure and/or flow reflects the result ("output"). Depending on the level of support, the ratio between the output and the input (i.e., 1/S) indicates the total "compliance" of the respiratory system of the patient P.

Figure 5A:
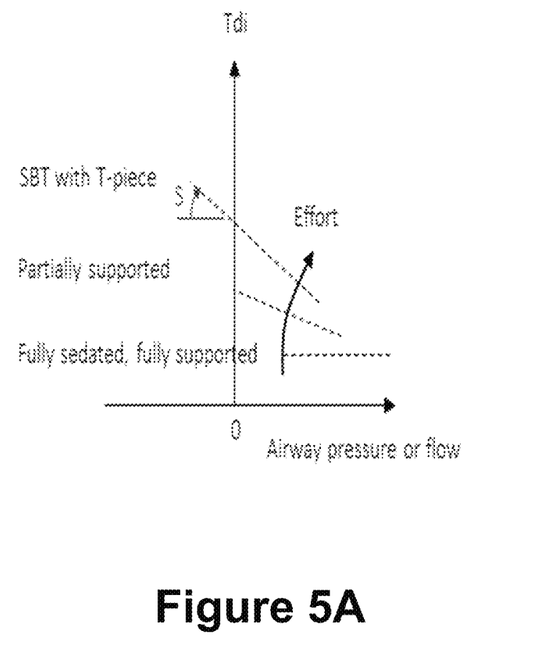
Figure 5B:
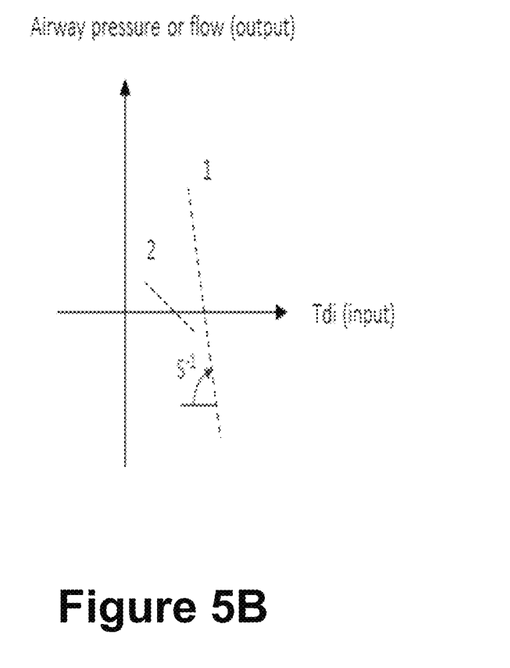

Examples of the use of the slope S of the linear regression relation between diaphragm thickness Tdi and airway pressure (or flow) to inform on the patient respiratory effort and effectiveness is shown in FIGS. 5A and 5B. FIG. 5A shows patient effort in different situations. Goligher (2015) mentions if there is no activity from the diaphragm, the thickness of the diaphragm does not change (i.e., a flat line with zero slope). If the pressure support goes down, the slope should go up. The more the slope goes up, the more responsive the patient P is to the mechanical ventilation therapy. Provided the end-tidal $CO_2$ does not go up due to respiratory (i.e., diaphragm) failure in which case the $CO_2$ starts pulling the muscle via chemoreceptors, and provided the sedation level stays constant. To monitor the impact of the respiration rate variation, additional indicators such as power of breathing (POB), POB over a liter of air (POB/L), work of breathing (WOB), and WOB over a liter of air WOB/L, can be used as additional inputs. FIG. 5B shows a surrogate for the efficiency of breathing in for example a spontaneous breathing test (SBT), where a first curve 1 is more efficient than second curve 2 (i.e., a larger pressure swing with less effort). In this case, the slope S of the second curve 2 is 1/S because the axes are swapped compared to FIG. 5A.

In some embodiments, instead of using the slope S (or the inverse 1/S), a change in slope ΔS when the level of support or sedation changes can be used to provide insight in the behavior and effectiveness of the diaphragm muscle activity as a function of the MV support of the patient P and sedation therapy of the patient P.

The parameters, S, 1/S, and ΔS can be displayed as the indication 30 on the display device 14 of the mechanical ventilator 2 to provide clinical decision support, such as distinguishing between active and passive (i.e., with the mechanical ventilator 2) breathing to guide sedation therapy, to indicate and monitor the level of sedation, to determine the optimal level of pressure support in PSV or K setting in PAV/PAV+ (where K is the percentage of unloading), to determine the weaning readiness before a spontaneous breathing test (SBT), to monitor lung mechanics for example in the case of lung disease (i.e., a steeper slope S means less flow, provided the MV settings are constant, to monitor the strength of a neuromuscular drive of the patient P, to detect phrenic nerve dysfunction or damage (for example, by placing a sensor on each side of the chest and sequentially paralyze on purpose the left and right nerve. In both situations the diaphragm should work the same. If not, one of the nerves is damaged), to determine whether a variation of slopes between breaths can be used as an indicator for asynchrony, and so forth. The parameter S or (1/S) could be relevant for monitoring CPAP home therapy where the patient is breathing spontaneously, and the ventilator keeps the pressure almost constant (i.e., S=ΔTdi/Δv).

If the patient P is breathing spontaneously, then a "compliance" of the respiratory system (what part of the muscle work is converted into airflow) can be measured. This ratio can be monitored in time and displayed to see how the patient's "respiratory motor" performs and evolves over time.

In some embodiments, the MV settings are constant. In other embodiments, the pressure and flow settings can be varied, or a controlled breathing maneuver can be carried out, while measuring a trend in Tdi or TFDI. This will provide further information on the status of the patient P and the therapy effect. For example, a strong response of the diaphragm muscle to a variation in pressure support or sedation indicates that the muscle is in a good condition and that the therapy is in a sensitive range (i.e., there is no over-treatment).

Referring back to FIG. 2, in some embodiments, at an operation 105, the mechanical ventilator 2 can be controlled to adjust one or more parameters of the mechanical ventilation therapy delivered to the patient based on the calculated diaphragm thickness metric. For example, the effort slope S and/or the maximum effort can be used to guide a respiratory muscle training program for the patient P. This program can be executed multiple times a day to restore and improve respiratory muscle strength. For example, the clinical team can select the maximum slope a patient can tolerate and for how long. The mechanical ventilator 2 can automatically change the support to increase/decrease respiratory activities as requested by the clinical team. As a safety feature, the mechanical ventilator 2 can monitor the respiratory rate, end-tidal CO2, SpO2 and other parameters to decide to switch to a backup mode and interrupt the training program.

At an optional operation 106, a responsiveness index (RI) of the patient P can be calculated as a ratio of a change in the compliance of the airway of the patient to a change in one or more mechanical ventilation settings of the mechanical ventilator 2. In some examples, the mechanical ventilator 2 can be controlled to adjust one or more parameters of the mechanical ventilation therapy delivered to the patient P based on the calculated responsiveness index. In other examples, the representation 30 can further include a representation of the calculated RI and displayed on the display device 14.

With the knowledge of the respiratory muscles' activities from diaphragmatic ultrasound or similar, and with the tuning of the support of the mechanical ventilator 2, the patient's responsiveness to such a change (i.e., a change in the slope S of the respiratory muscle activities) can be monitored. This could be a change in slope of the respiratory muscle activities divided by the change in support (pressure support ventilation PSV, proportional assist ventilation PAV, same here PAV+, pressure regulated volume control PRVC, neurally adjusted ventilatory assist NAVA etc.) according to RI=ΔS/Δsupport, where Δsupport represents a change in the level of support in a change in pressure p or the change in volume/flow v. The RI could be used to guide the sedation strategy in an open or closed-loop solution, i.e., by controlling a sedation device configured to provide a sedative to the patient P. Additional input such as end-tidal CO2, blood gas analysis, minute ventilation, and ventilator settings, can be used by the electronic controller 13 to ensure safe operation thereof.

For anesthesiologists, the RI can potentially be used to quantify the sedation level. Commonly, the sedation level is measured using the Ramsay Sedation Scale, which is a qualitative measure. It divides a patient's level of sedation into six categories ranging from severe agitation to deep coma. Typically, the clinician observes the patients' response to commands or tactile and auditory stimuli. A quantitative measure is less prone to interpretation and the automatic measurement of RI could promote the usage and application of sedation scoring in mechanical ventilation therapy.

In some embodiments, a medical professional may want to check on a status of the patient P. This can be enabled by checking the slope S or slope change ΔS as displayed on the display device 14 on a regular basis (for example every 12 hours) by pressing and/or holding a button on the mechanical ventilator 2. Pressing the button takes the support away for a couple of minutes. This can reveal the RI.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A diaphragm measurement device, comprising:
   at least one electronic processor programmed to perform a diaphragm measurement method including:
   receiving ultrasound imaging data of a dimension of a diaphragm of a patient during inspiration and expiration while the patient undergoes mechanical ventilation therapy with an associated mechanical ventilator;

receiving respiratory data of the patient during inspiration and expiration while the patient undergoes the mechanical ventilation therapy;

calculating a diaphragm thickness metric based on the received ultrasound imaging data of the diaphragm of the patient and the received respiratory data;

displaying, on a display device, a representation of the calculated diaphragm thickness metric; and controlling the associated mechanical ventilator to adjust one or more parameters of the mechanical ventilation therapy delivered to the patient based on the calculated diaphragm thickness metric;

wherein the respiratory data of the patient comprises one of an airway pressure or airway flow in an airway of the patient, and the at least one electronic processor is further programmed to calculate the diaphragm thickness metric based on the airway pressure or the airway flow; and wherein the respiratory data comprises a mean airway pressure value or a mean airway flow value at an end of inspiration and at an end of expiration.

2. A diaphragm measurement device, comprising:

at least one electronic processor programmed to perform a diaphragm measurement method including:

receiving ultrasound imaging data of a dimension of a diaphragm of a patient during inspiration and expiration while the patient undergoes mechanical ventilation therapy with an associated mechanical ventilator;

receiving respiratory data of the patient during inspiration and expiration while the patient undergoes the mechanical ventilation therapy;

calculating a diaphragm thickness metric based on the received ultrasound imaging data of the diaphragm of the patient and the received respiratory data;

displaying, on a display device, a representation of the calculated diaphragm thickness metric; and controlling the associated mechanical ventilator to adjust one or more parameters of the mechanical ventilation therapy delivered to the patient based on the calculated diaphragm thickness metric;

wherein the respiratory data of the patient comprises one of an airway pressure or airway flow in an airway of the patient, and the at least one electronic processor is further programmed to calculate the diaphragm thickness metric based on the airway pressure or the airway flow; and wherein the respiratory data comprises a maximum airway pressure value or a maximum airway flow value and a minimum airway pressure value or a minimum airway flow value at an end of inspiration and at an end of expiration.

3. A diaphragm measurement device, comprising:

at least one electronic processor programmed to perform a diaphragm measurement method including:

receiving ultrasound imaging data of a dimension of a diaphragm of a patient during inspiration and expiration while the patient undergoes mechanical ventilation therapy with an associated mechanical ventilator;

receiving respiratory data of the patient during inspiration and expiration while the patient undergoes the mechanical ventilation therapy;

calculating a diaphragm thickness metric based on the received ultrasound imaging data of the diaphragm of the patient and the received respiratory data;

displaying, on a display device, a representation of the calculated diaphragm thickness metric; and controlling the associated mechanical ventilator to adjust one or more parameters of the mechanical ventilation therapy delivered to the patient based on the calculated diaphragm thickness metric;

wherein the at least one electronic processor is further programmed to calculate the diaphragm thickness metric as a ratio of a diaphragmatic thickness of the diaphragm and an airway pressure in an airway of the patient.

4. A diaphragm measurement device, comprising:

at least one electronic processor programmed to perform a diaphragm measurement method including:

receiving ultrasound imaging data of a dimension of a diaphragm of a patient during inspiration and expiration while the patient undergoes mechanical ventilation therapy with an associated mechanical ventilator;

receiving respiratory data of the patient during inspiration and expiration while the patient undergoes the mechanical ventilation therapy;

calculating a diaphragm thickness metric based on the received ultrasound imaging data of the diaphragm of the patient and the received respiratory data;

displaying, on a display device, a representation of the calculated diaphragm thickness metric; and controlling the associated mechanical ventilator to adjust one or more parameters of the mechanical ventilation therapy delivered to the patient based on the calculated diaphragm thickness metric;

wherein the at least one electronic processor is further programmed to calculate the diaphragm thickness metric as a ratio of a diaphragmatic thickness of the diaphragm and an airway flow in an airway of the patient.

5. The device of claim 4, wherein the at least one electronic processor is further programmed to:

calculate a responsiveness index of the patient as a ratio of a change in a compliance of the airway of the patient to a change in one or more mechanical ventilation settings of the associated mechanical ventilator.

6. The device of claim 5, wherein the at least one electronic processor is further programmed to:

control the associated mechanical ventilator to adjust one or more parameters of the mechanical ventilation therapy delivered to the patient based on the calculated responsiveness index.

7. The device of claim 6, wherein the at least one electronic processor is further programmed to:

display, on the display device, a representation of the calculated responsiveness index.

8. A diaphragm measurement method comprising, with at least one electronic controller:

receiving ultrasound imaging data of a dimension of a diaphragm of a patient during inspiration and expiration while the patient undergoes mechanical ventilation therapy with a mechanical ventilator;

receiving respiratory data of the patient during inspiration and expiration while the patient undergoes the mechanical ventilation therapy;

calculating a diaphragm thickness metric based on the received ultrasound imaging data of the diaphragm of the patient and the received respiratory data;

calculating a responsiveness index of the patient as a ratio of a change in a compliance of an airway of the patient to a change in one or more mechanical ventilation settings of the mechanical ventilator delivering the mechanical ventilation therapy to the patient; and adjusting the mechanical ventilation therapy based on the calculated responsiveness index.

9. The method of claim 8, further including:

displaying, on a display device, a representation of the calculated diaphragm thickness metric.

\* \* \* \* \*